Figure 1:
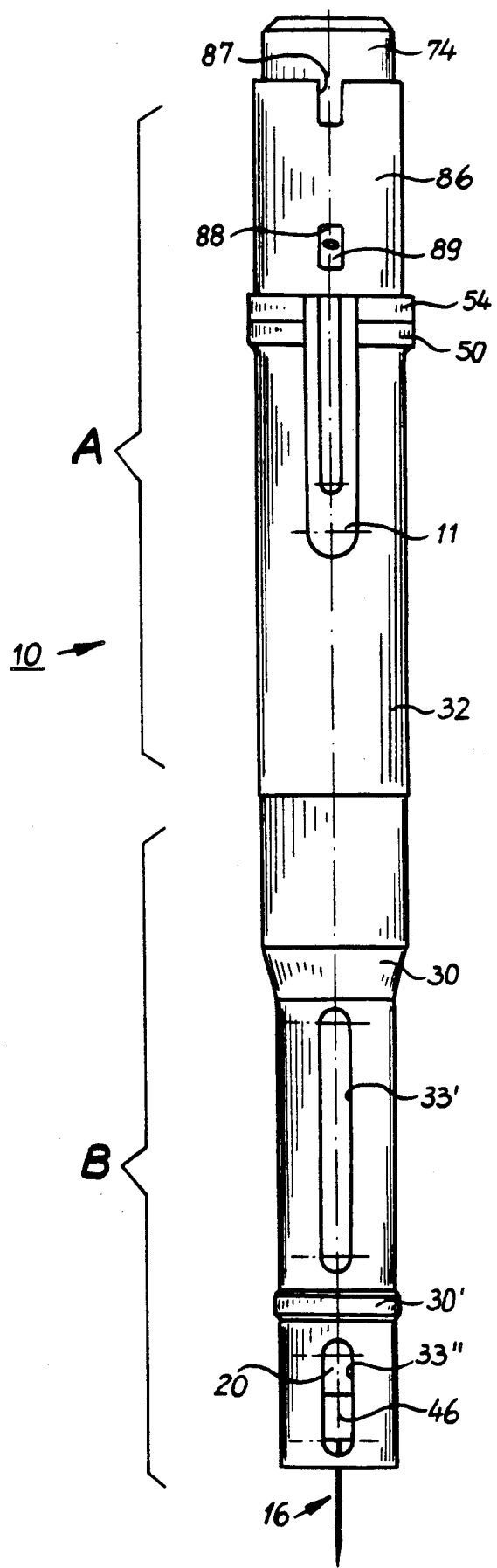

United States Patent [19]
Bechtold et al.

[11] Patent Number: 5,092,842
[45] Date of Patent: Mar. 3, 1992

[54] INJECTION DEVICE WITH A COCKING ELEMENT AND A SECOND SETTING ELEMENT

[75] Inventors: Herbert Bechtold, Ehningen; Jochen Gabriel, Stuttgart, both of Fed. Rep. of Germany

[73] Assignee: Wilhelm Haselmeier GmbH & Co., Stuttgart, Fed. Rep. of Germany

[21] Appl. No.: 435,422

[22] PCT Filed: May 5, 1988

[86] PCT No.: PCT/EP88/00375

§ 371 Date: Nov. 3, 1989

§ 102(e) Date: Nov. 3, 1989

[87] PCT Pub. No.: WO88/08725

PCT Pub. Date: Nov. 17, 1988

[30] Foreign Application Priority Data

May 8, 1987 [DE] Fed. Rep. of Germany ....... 3715258

[51] Int. Cl.⁵ .............................................. A61M 5/20
[52] U.S. Cl. ..................................... 604/135; 604/209; 604/211; 604/232
[58] Field of Search .......................... 604/68–72, 604/131, 134–139, 200, 207–209, 211, 220, 224, 232, 187

[56] References Cited

U.S. PATENT DOCUMENTS

| | | |
|---|---|---|
| 2,565,081 | 8/1951 | Maynes . |
| 2,632,445 | 3/1953 | Kas, Sr. ............................ 604/209 |
| 2,737,946 | 3/1956 | Hein, Jr. ........................... 604/70 |
| 3,526,225 | 9/1970 | Isobe ................................ 604/71 |
| 3,815,785 | 6/1974 | Gilmont . |
| 3,882,863 | 5/1975 | Sarnoff et al. ................... 604/136 |
| 4,103,684 | 8/1978 | Ismach ............................. 604/71 |
| 4,258,713 | 3/1981 | Wardlaw .......................... 604/139 |
| 4,498,904 | 2/1985 | Turner et al. . |
| 4,526,294 | 7/1985 | Hirschmann et al. ............ 222/47 |
| 4,530,695 | 7/1985 | Phillips et al. .................... 604/184 |
| 4,592,742 | 6/1986 | Landau ............................ 604/71 |
| 4,717,383 | 1/1988 | Phillips et al. . |
| 4,850,967 | 7/1989 | Cosmai ............................ 604/68 |
| 4,883,472 | 11/1989 | Michel ............................ 604/208 |
| 4,936,833 | 6/1990 | Sams ............................... 604/232 |
| 4,973,318 | 11/1990 | Holm et al. ..................... 604/208 |
| 4,983,164 | 1/1991 | Hoak et al. ..................... 604/87 |

FOREIGN PATENT DOCUMENTS 720448 4/1973 Fed. Rep. of Germany .
WO87/02895 5/1987 PCT Int'l Appl. .

Primary Examiner—John D. Yasko
Assistant Examiner—Adam J. Cermak
Attorney, Agent, or Firm—Frishauf, Holtz, Goodman & Woodward

[57] ABSTRACT

The injection device described comprises a loading element (74) which can be moved longitudinally for loading purposes and is rotatable for the purpose of setting the injection dose. Associated with this loading element (74) is a second setting element (86). The latter allows a judicious internal combination of the information supplied by the position of the loading element (74) and of the second setting element (86). The patient can effect several individually-dosed injections from a single container.

22 Claims, 12 Drawing Sheets

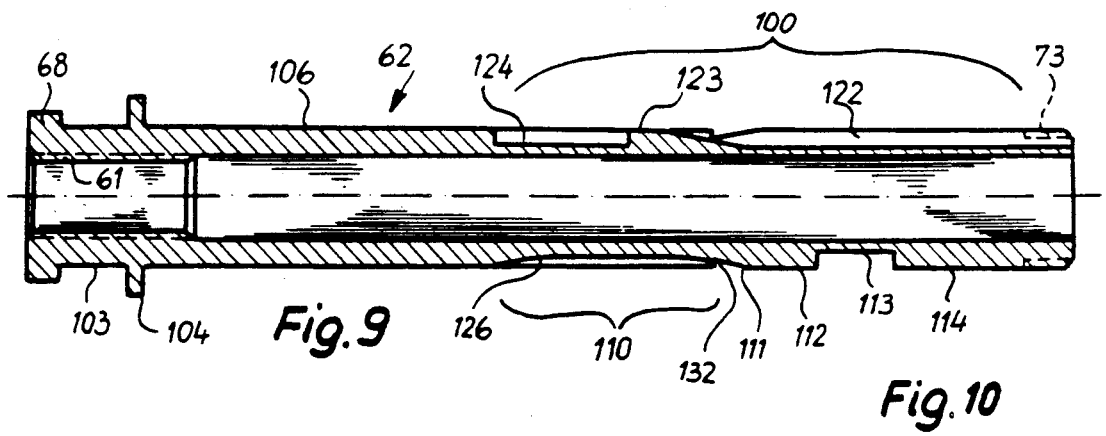
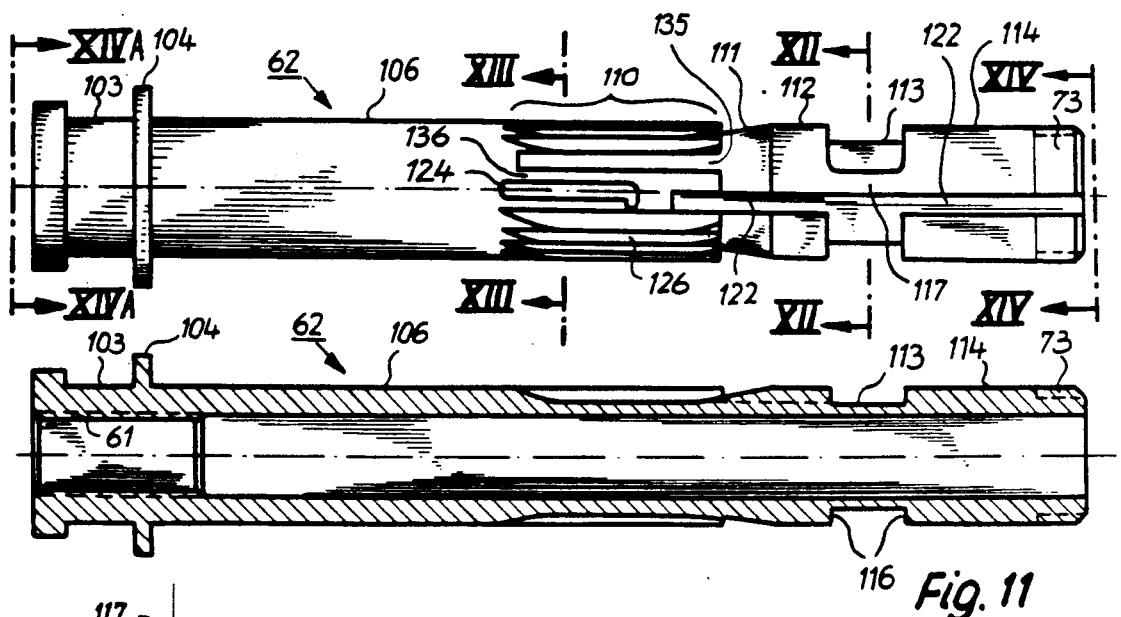
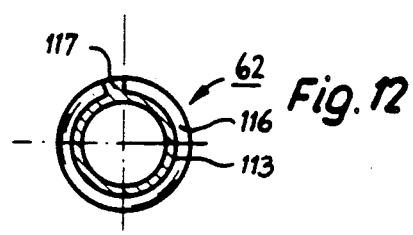
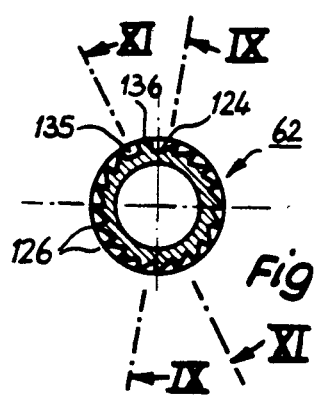
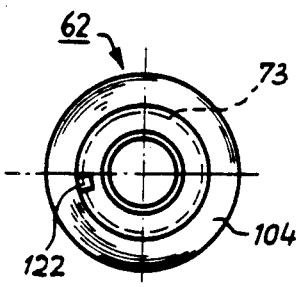
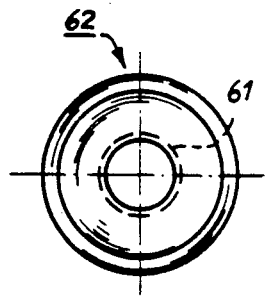

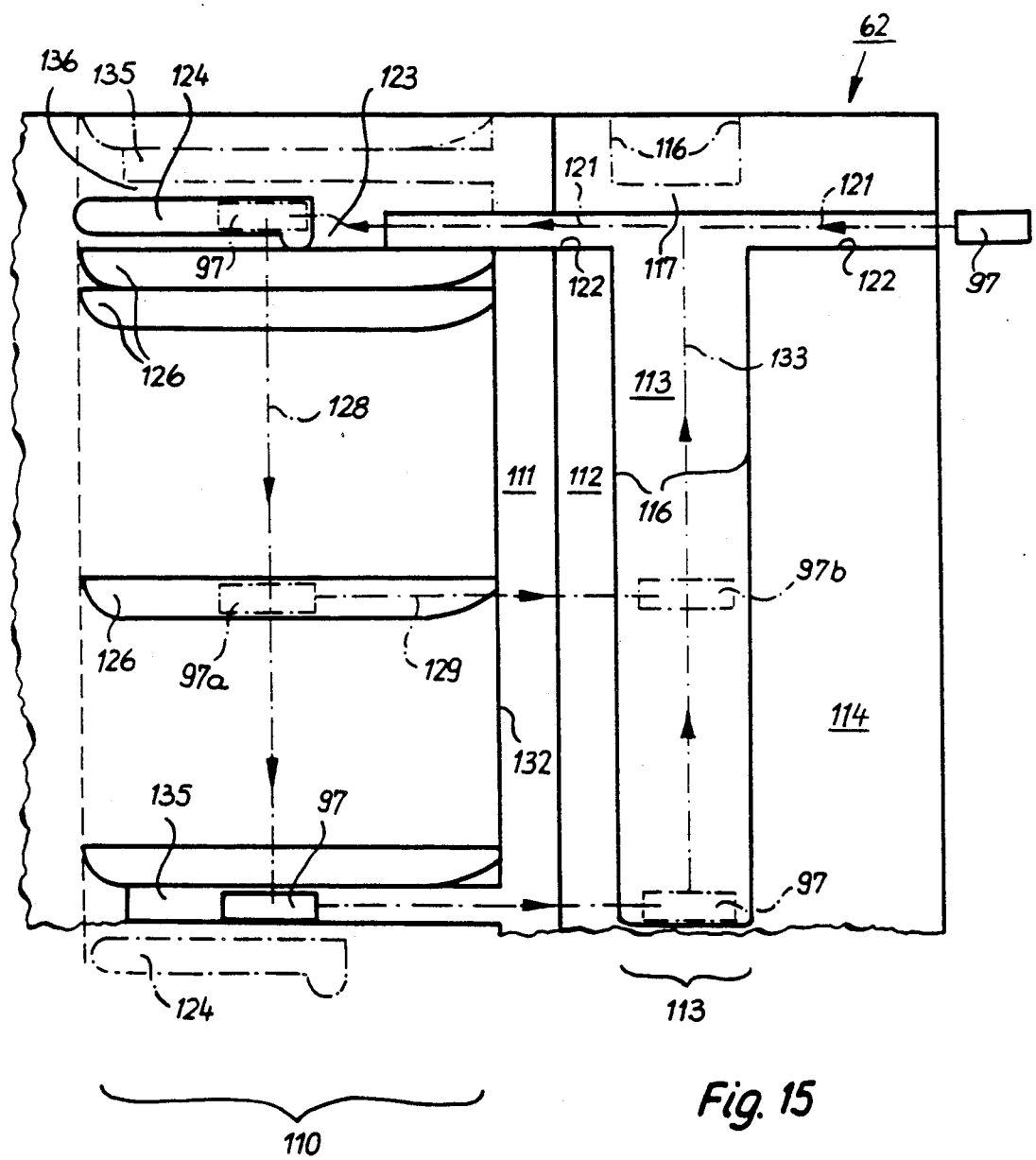

INJECTION DEVICE WITH A COCKING ELEMENT AND A SECOND SETTING ELEMENT

FIELD OF THE INVENTION

The invention relates to an injection device having a mechanism for effecting an injection process, the mechanism being movable by a cocking means counter to the force of a spring into a cocking position, from which it can be released to effect an injection process, so as to act upon a wall, in particular a piston, of a container containing fluid to be injected.

BACKGROUND

U.S. Pat. No. 4,194,505 discloses an injection device used primarily for injecting insulin. It has a mechanism for effecting an injection process that is movable counter to the force of a spring into a cocked position, out of which it can be released to act upon the piston of a cartridge containing insulin. An adjusting element on the housing of this known injection device is used as a stop for the aforementioned mechanism and makes it possible to vary the effective length of the mechanism and hence the injection dose, within certain limits. A scale with which the adjusting element can be set to a desired value is provided on the housing. The known device is embodied to hold special cartridges, which contain a certain quantity of insulin, such as 20 units. If the patient needs only 17 units, he can make a setting on the adjusting element accordingly. To do so, he first sets the maximum dose, which is equivalent to a zero line on the scale of the device. Beginning there, he adjusts by three lines on the scale, corresponding to the three units that he does not want to inject, using the adjusting element. This adjusts the stop on the housing for the movable mechanism. Next, the patient initiates the injection, whereupon the needle is first inserted into the patient and then the desired dose of insulin is injected from the cartridge. This device is complicated to use: Cartridges of various doses are needed for it, namely cartridges containing 10, 20, 30, 40, 50 and 60 units of insulin. If the patient is blind, he can easily mistake such cartridges for one another, and the danger then exists that he may inject too much insulin. The calculations that must be made in using the device are not exactly simple either, and may be too difficult for some patients. In so-called intensified insulin therapy, the patient must inject a different amount of insulin after each meal, and mistakes in calculation are easy to make; or the patient may simply reuse the old setting for the device. If the patient needs 8 units of insulin after breakfast, 15 units after lunch and 12 units after dinner, for instance, then with this known device he has to use one 10-unit cartridge for breakfast and set the device to minus two units. For lunch and dinner, he has to use a 20-unit cartridge, setting the device to minus five units at noon and to minus eight units in the evening. This all requires great care and may easily lead to mistakes.

A so-called rumen injector is also known from German Patent 3 527 066. In this device, the piston rod of the injection piston has a handle on its free end, and an adjustable stop provided on the device facing the handle limits the motion of the handle and thereby determines the injection dose. With this device, the veterinarian inserts the hypodermic needle manually into the animal, and the insertion initiates an automatic injection process, in which a spring presses the piston rod so far into the injection cylinder that the handle strikes the aforementioned stop. The disadvantage of this device is that the injection cylinder has to be reloaded before each injection, which does not allow the use of cartridges or other containers holding more than one dose of the fluid to be injected.

From European Disclosure Document Al 0 058 536, an injection device is known with which a patient can inject more than one dose of insulin from one cartridge. To do so, he adjusts the desired insulin dose by turning an adjusting wheel, then inserts the needle into himself, and then turns the pre-adjusting wheel back to its zero position. This screws a threaded part out of a sleeve, presses it against the piston in the cartridge, and forces insulin out of the cartridge into the patient through the needle. However, this has the disadvantage that the device can be used only on the front part of the body, while with so-called intensified insulin therapy one is forced in practice to make injections on the back part of the body as well, to avoid hematomas and cornification from overly frequent injection at the same site. Also, injection by manually turning a pre-adjusting wheel is very painful for some patients.

Such injection devices are complicated devices. The patient must therefore be carefully instructed, usually in a hospital, in their use. In addition, the use of such devices should be made as simple and understandable as possible, so that the patient will not find the device burdensome to use and will continue his therapy regularly and without making mistakes.

THE INVENTION

It is an object to provide an injection device that evaluates various kinds of information items of the device.

Briefly, from the relative position of a first setting element and another, or second element, the control arrangement receives information which is evaluated in control arrangement to make the device safer to use and—as much as possible, given the small size of such a device—error-free. In this way, a sort of internal computer in the form of this control arrangement is obtained; it evaluates the information supplied to it from the positions of the first and second elements and processes the information into corresponding "commands", which are adapted to prevent incorrect use by the patient.

According to a feature of the invention, the control arrangement has an engagement element. After the device is cocked with a cocking element, the engagement element is in engagement with a first portion of a counterpart element to permit setting of the dosage only before the injection process, i.e. when an injection element is in distal position.

According to another feature of the invention, the second portion of the counterpart element has a stop for engaging the engagement element and thus limits the relative rotation between the first setting element, which is used simultaneously as a cocking element, and the second or other element, so that after the injection the patient can easily readjust the second element up to this stop, even if his vision is poor, for example.

In accordance with another feature of the invention, the second portion of the counterpart element has a control recess for the engagement of the engagement element. This control recess prevents recocking of the cocking element after the injection, unless the patient has first set a certain relative rotational position between the two setting elements This reminds the patient that he has to establish a certain setting before cocking the device; for instance it reminds him that he has to set the scale display of his device to zero, because otherwise he cannot cock the device at all. This makes it difficult or impossible to use the device incorrectly. A particularly advantageous embodiment of the second portion of the counterpart element is the subject of claim 4.

In the subject of claim 5, the first portion of the counterpart element has ratchet teeth for engagement with the engagement element. This enables the user to set the dose only after the device is already cocked, and even a visually impaired or blind patient can perform the setting. Setting the dose only after cocking has the advantage that the patient cannot use the dose setting from the previous injection. This is especially important in intensified insulin therapy, because in such therapy, quite variable amounts of insulin must be injected depending on the time of day. The ratchet teeth are preferably embodied in accordance with claim 6, to enable the engagement element to slide axially out of the ratchet teeth during the injection process.

In the subject of claim 7, the first portion of the counterpart element has a blocking device which in a predetermined relative rotational position between the engagement element and the counterpart element blocks any injection process. This prevents the patient from initiating an injection process immediately after cocking the device without having first set an injection dose. If the patient tries to initiate an injection directly after cocking the device, he is reminded that he has to set the correct injection dose first, after cocking the device.

In the subject of claim 8, the first portion of the counterpart element has a stop for engagement with the engagement element. This places an upper limit on the setting of the injection dose and prevents a confused patient, for example, from setting a highly excessive injection dose.

The control recesses and the engagement element can be so formed that in the setting process—in the cocked state of the injection device—they permit only an increase of the injection dose. This prevents a visually impaired patient, for example, from first increasing his dose, then reducing it, and finally not knowing what setting he actually arrived at.

A scale display can be provided, indicating the relative setting of the elements. This enables the set injection does to be displayed in a very simple manner. After the injection the scale can be reset to zero. The patient is thus spared complicated calculations that are rife with opportunity for error.

The second element is highly preferably and advantageously connected to the housing via a slip coupling. This makes the second setting element infinitely adjustable. Naturally, a ratchet mechanism could be used instead of a slip coupling, within the scope of the invention, but in that case readjustment of the second setting element would be possible only in discrete increments.

Particularly advantageously, and in accordance with this slip coupling (or ratchet mechanism, for example) is so formed that the second element—which during operation must also form a stop for the rotational motions of the cocking element—cannot be turned until after a not-inconsiderable breakaway torque has been overcome. Thus the second element also performs multiple functions, in a very simple, space-saving manner.

It is particularly advantageous if the displayed scale value is visible in both the cocked and the uncocked state, because then the set injection dose is initially "stored in memory", and the patient can look again during lunch, for example, and see how much insulin he injected that morning. This seemingly simple provision is lacking in known devices, and represents a major advance in safety.

Locating the second element to at lest partly surround the cocking element, prevents the finger of the user from being caught and pinched during the injection process, something that is often quite painful A guide element can be provided which performs several functions at the same time and can be assembled very easily.

Fully automatic injection is possible; that is, the patient merely places the cocked, correctly set injection device at the desired site on the body, actuates a release, and then both the insertion of the hypodermic needle and the injection of the set dose proceed automatically. This allows injections to be given on the back as well and is therefore especially important for so-called intensified insulin therapy.

Figure 2:
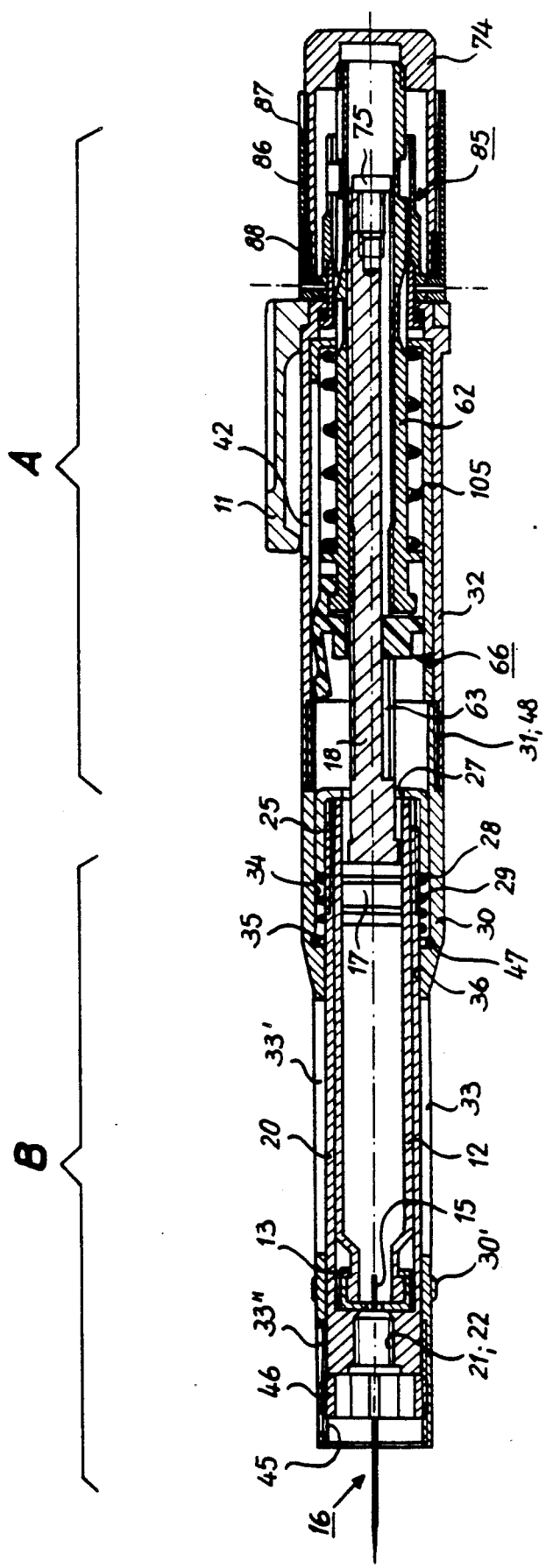
Figure 3:
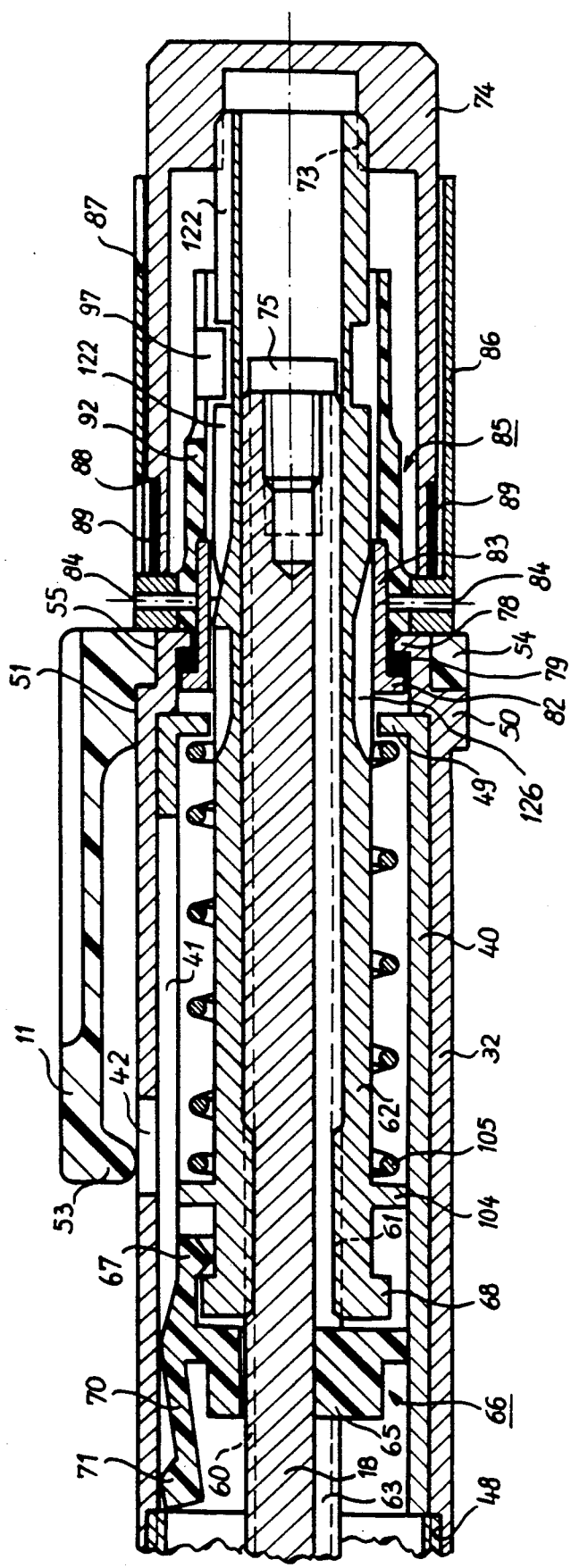
Figure 4:
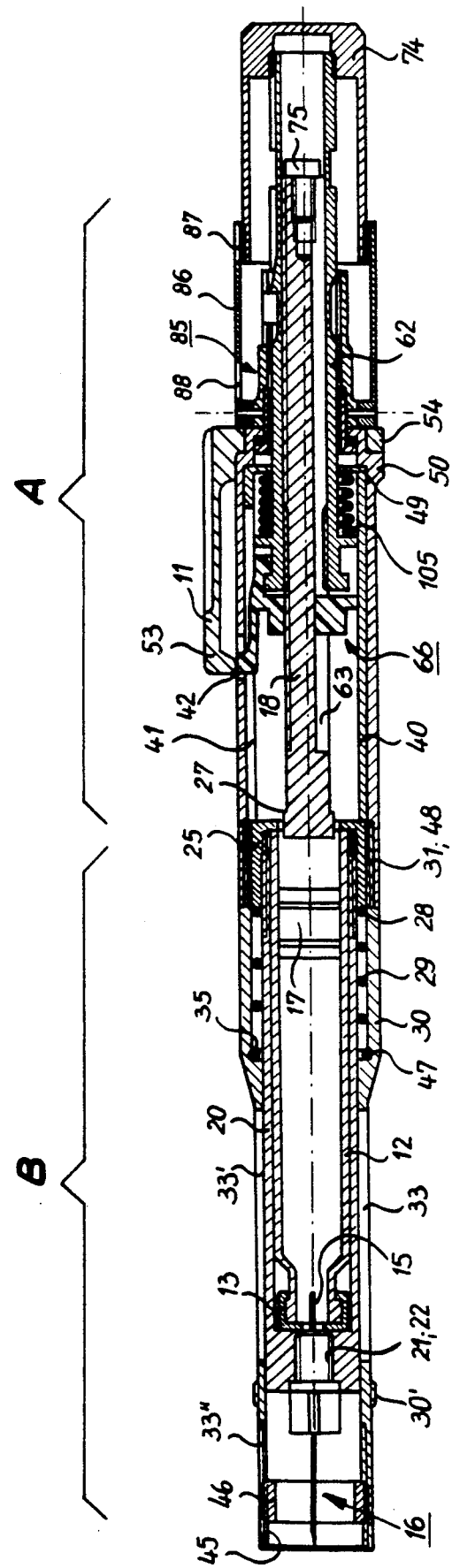
Figure 5:
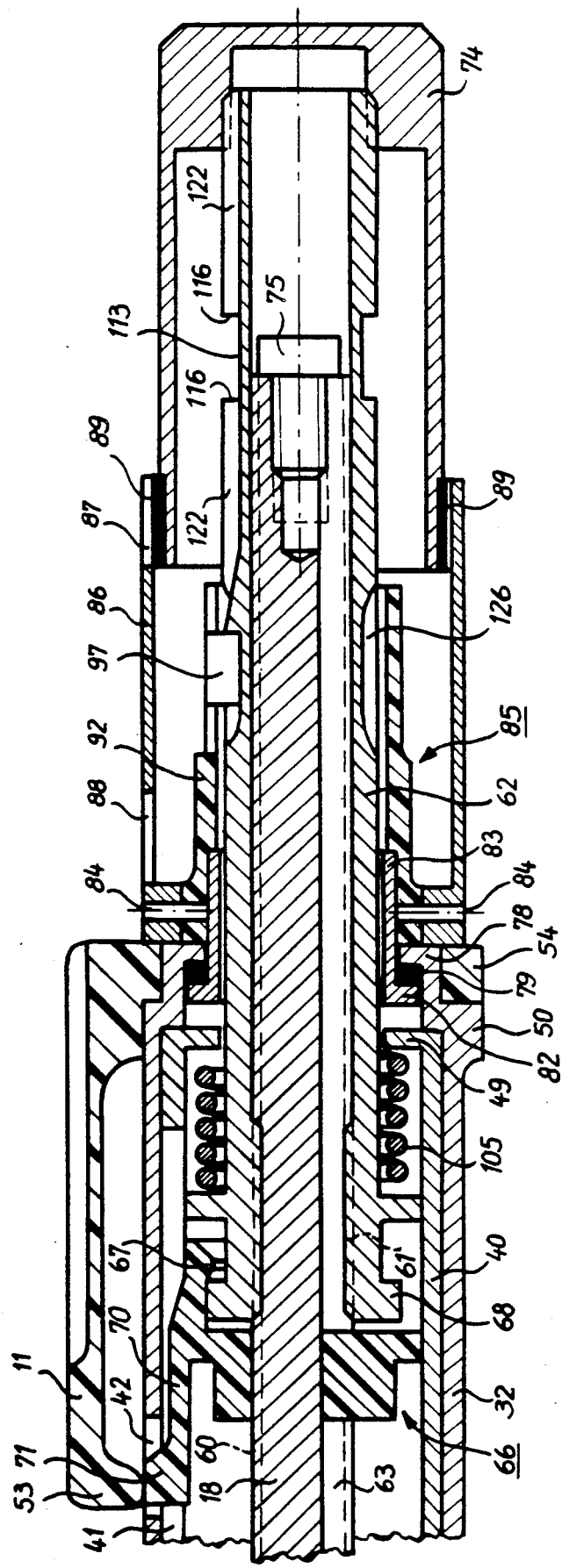
Figure 6:
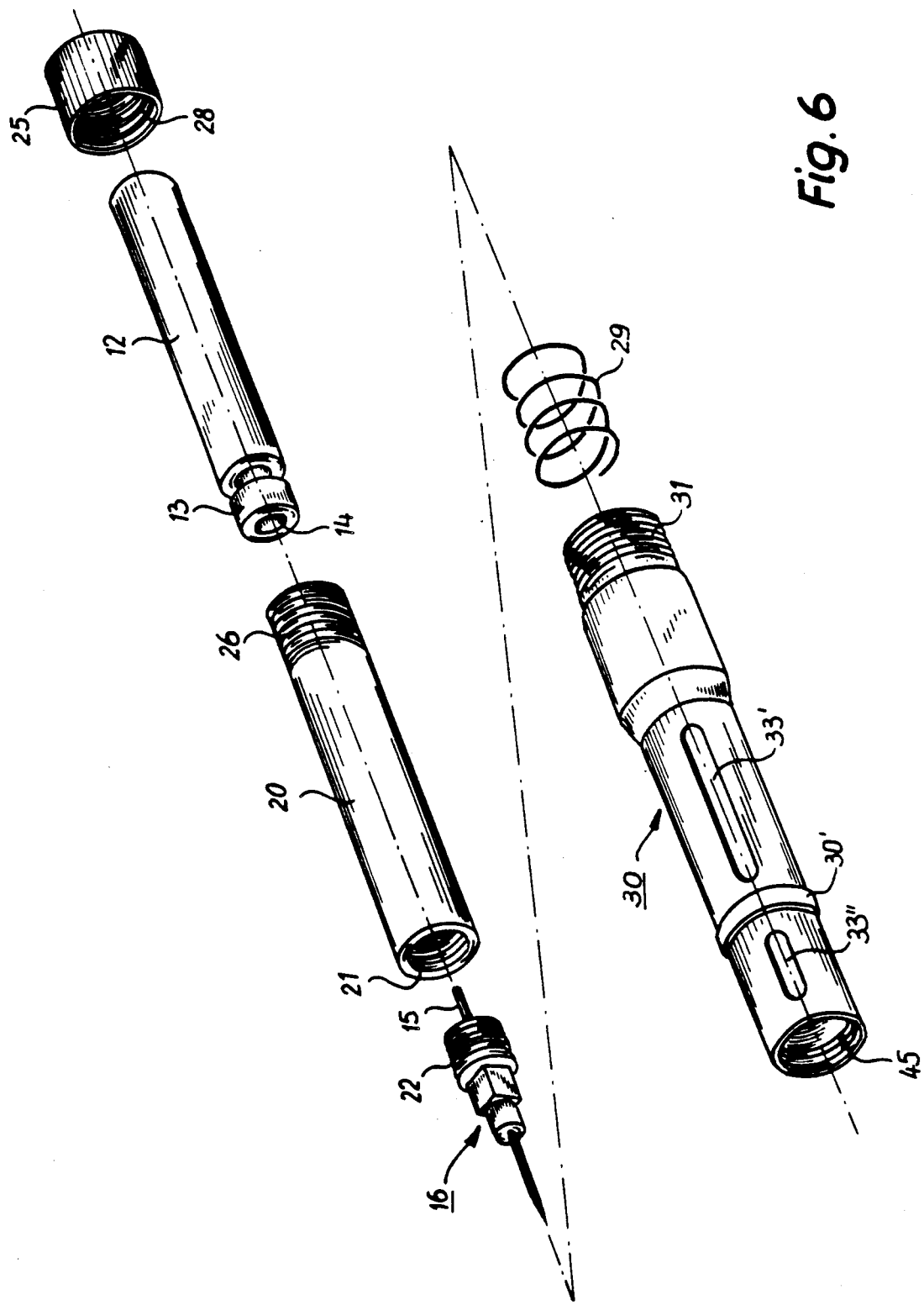
Figure 7:
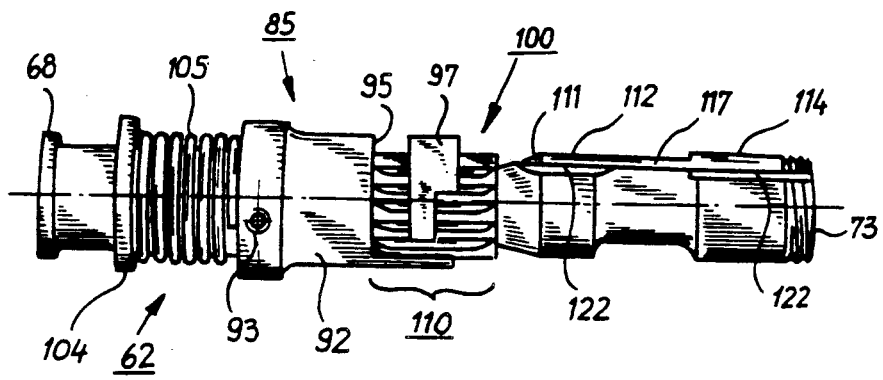
Figure 8:
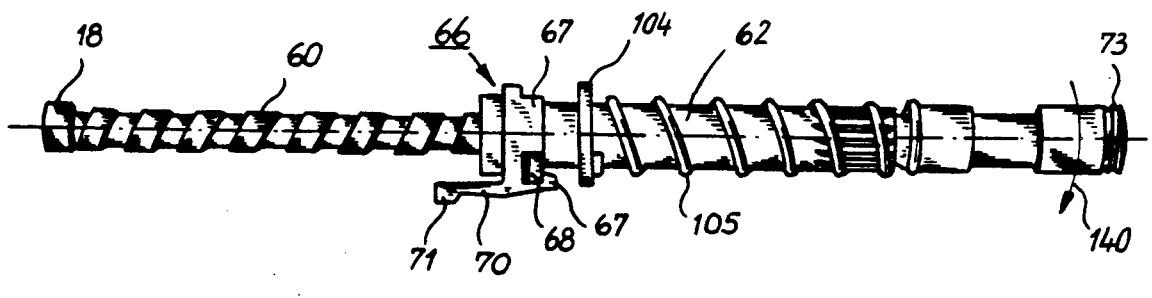
Figure 16:
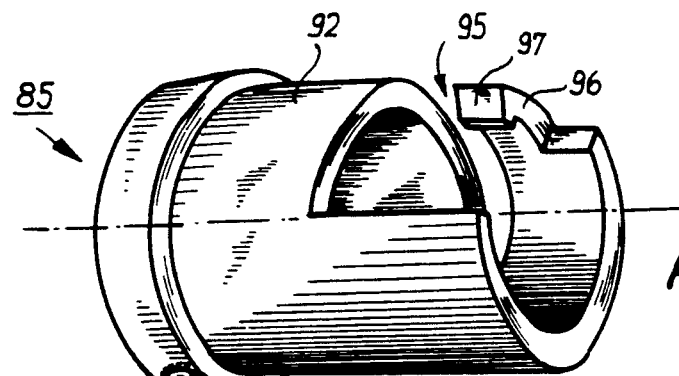
Figure 17:
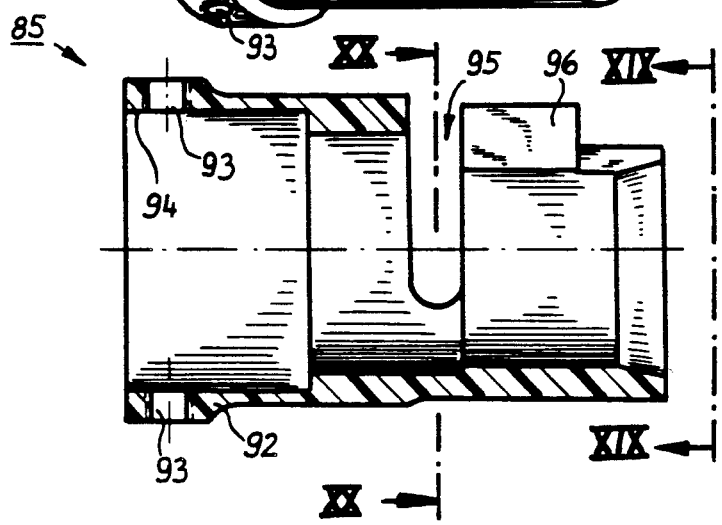
Figure 18:
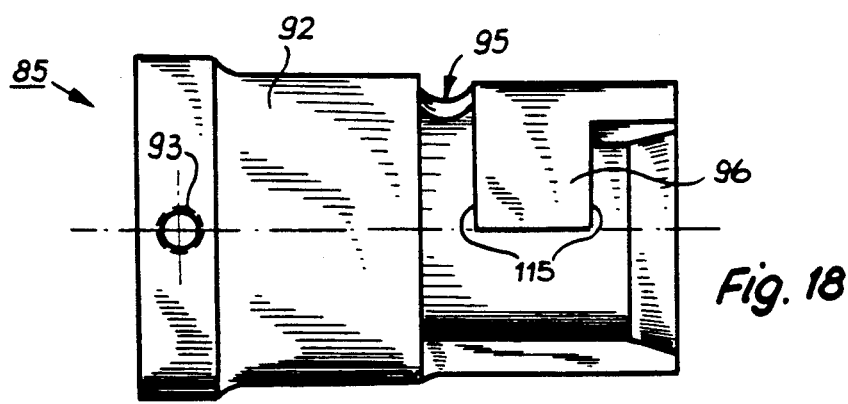
Figure 19:
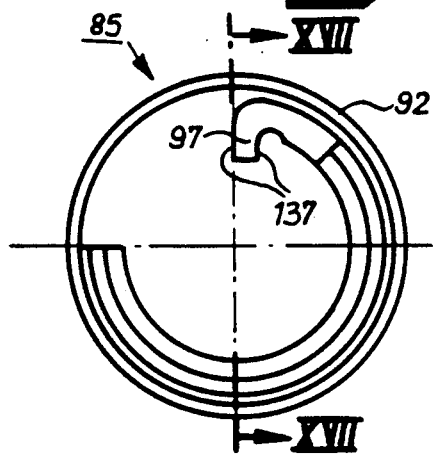
Figure 20:
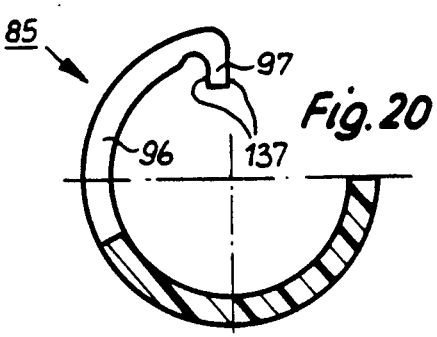
Figure 23:
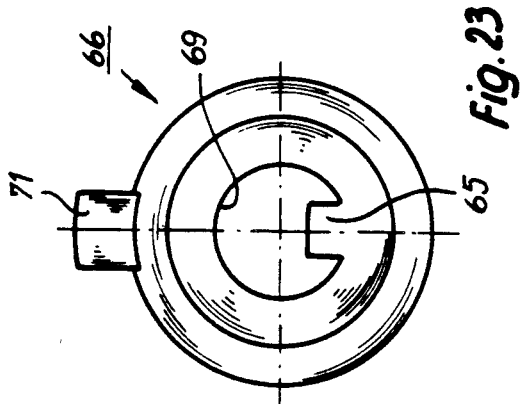
Figure 22:
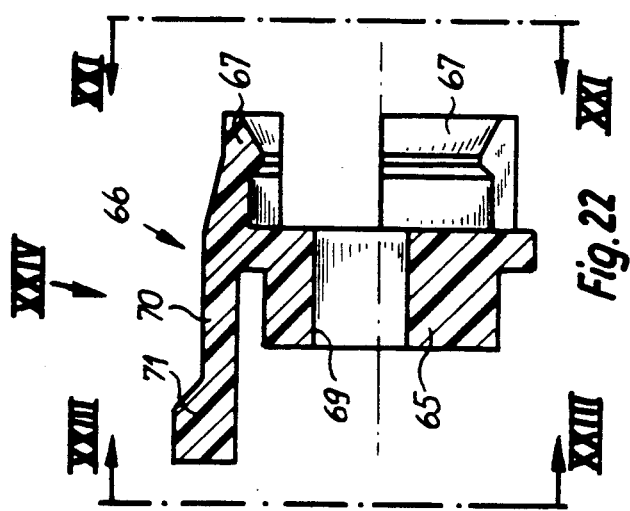
Figure 24:
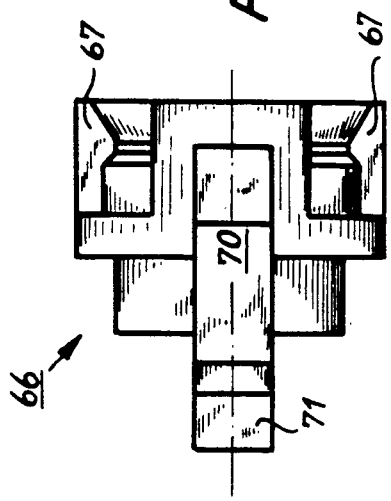
Figure 21:
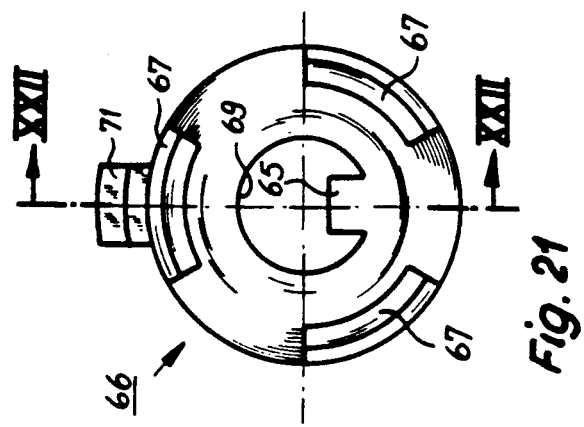
Figure 25:
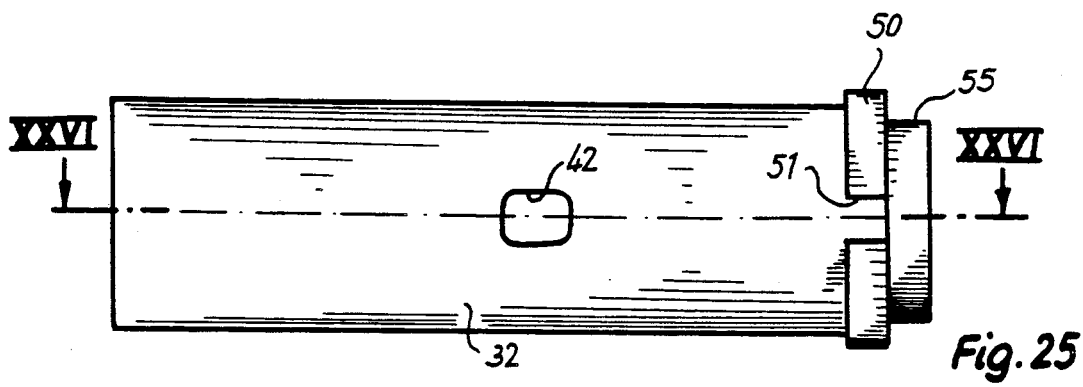
Figure 26:
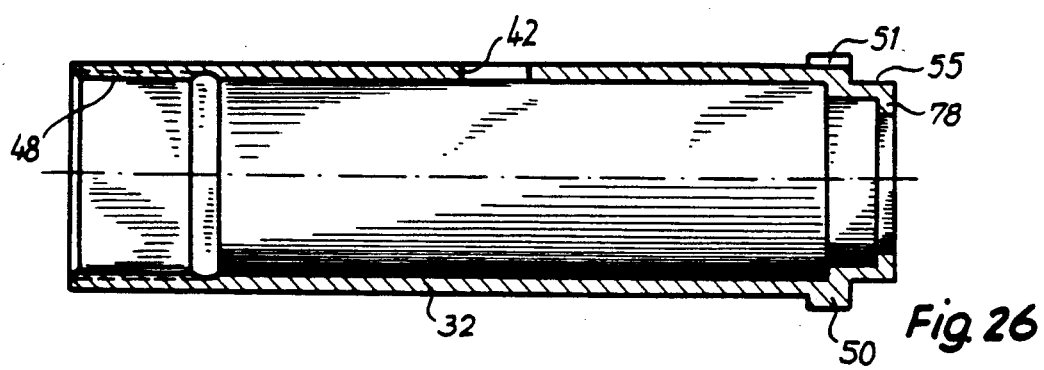
Figure 27:
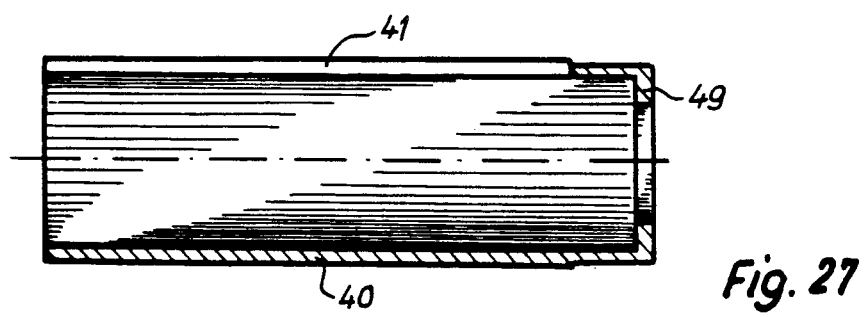
Figure 28:
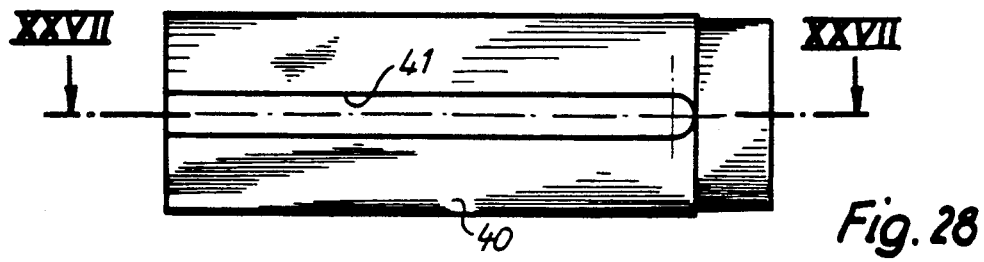

FIG. 1, a side view of an injection device according to the invention, seen on an enlarged scale and in the position after an injection has been given, seen from above;

FIG. 2, a view similar to FIG. 1, but rotated by 90° relative to it, in longitudinal section;

FIG. 3, a detail of FIG. 2, on a greatly enlarged scale;

FIG. 4, a longitudinal section through the injection device similar to FIG. 2, but in the cocked state, i.e., before the injection;

FIG. 5, a detail of FIG. 4, on a greatly enlarged scale;

FIG. 6, an exploded three-dimensional view of the so-called B part of the injection device, which is used to hold the cartridge containing the substance to be injected;

FIG. 7, a three-dimensional view of the control portion for controlling the injection quantity;

FIG. 8, a three-dimensional view, on a smaller scale than that of FIG. 7 of the tappet, which is adjustable in length;

FIG. 9, a longitudinal section through an adjusting sleeve used to set the injection quantity, taken along the line IX—IX of FIG. 13;

FIG. 10, a plan view on the adjusting sleeve of FIG. 9;

FIG. 11, a longitudinal section through the adjusting sleeve of FIG. 9 and 10, taken along the line XI—XI of FIG. 13;

FIG. 12, a section along the line XII—XII of FIG. 10;

FIG. 13, a section along the line XIII—XIII of FIG. 10;

FIG. 14, a side view of the adjusting sleeve, taken along the line XIV—XIV of FIG. 10;

FIG. 14A, a side view of the adjusting sleeve, taken along the line XIVA—XIVA of FIG. 10;

FIG. 15, a schematic diagram in the form of a developed view of the adjusting sleeve, for explaining the invention;

FIG. 16, a three-dimensional view of a ratchet device used in setting the injection quantity, on a greatly enlarged scale;

FIG. 17, a longitudinal section through the ratchet device of FIG. 16, taken along the line XVII—XVII of FIG. 19;

FIG. 18, a lateral top view on the ratchet device of FIGS. 16 and 17;

FIG. 19, a view along the line XIX—XIX of FIG. 17;

FIG. 20, a section along the line XX—XX of FIG. 17;

FIG. 21, a side view of a plastic part providing longitudinal guidance for the tappet, seen along the line XXI—XXI of FIG. 22;

FIG. 22, a longitudinal section along the line XXII—XXII of FIG. 21;

FIG. 23, a side view seen along the line XXIII—XXIII of FIG. 22;

FIG. 24, a top view along the arrow XXIV in FIG. 22;

FIG. 25, a top view of the rear (distal) housing part, showing the window provided in it that is used in initiating the injection process;

FIG. 26, a longitudinal section along the line XXVI—XXVI of FIG. 25;

FIG. 27, a longitudinal section through a sleevelike part that is inserted into the rear housing part shown in FIGS. 25 and 26, taken along the line XXVII—XXVII of FIG. 28; and FIG. 28, a plan view of the sleevelike part of FIG. 27.

FIG. 1 shows an injection device 10 according to the invention, in the position after an injection. The device is approximately the shape of an oversize fountain pen. It has a fastening clip 11, of the shape known in fountain pens, on its side. This clip 11 is also used as an initiating element for triggering the injection.

The injection device 10 has a part A, which is used both to set the quantity of fluid to be injected and to carry out the injection and is shown on a greatly enlarged scale in FIGS. 3 and 5, for the sake of easier comprehension.

The injection device 10 also has a part B, which is used to hold a container 12 (FIGS. 2, 4, 6), or cartridge, holding the fluid to be injected. This part B is shown in an exploded three-dimensional view in FIG. 6.

As seen in FIGS. 2, 4 and 6, the container 12 is in the form of an elongated cylindrical glass tube that tapers at the proximal end, that is, the end toward the patient, and is provided there with a crimped-on aluminum cap 13, in the middle of which is a thin rubber membrane 14 (see FIG. 6) that can be punctured by the distal end 15 of an injection needle, or hypodermic needle, 16. Such containers holding insulin are sold under the trademark "Penfill" by Novo Industri AB of Denmark, for instance. In the glass tube 12 is a displaceable piston 17, which may for instance be made from a suitable rubber and which can be displaced in the proximal direction, under the influence of a tappet or injecting plunger 18 (FIGS. 2-5), in order to effect an injection.

A holder sleeve 20 used to hold the container 12 is provided on its proximal end with a female thread 21, which is used to receive the corresponding male thread 22 of the injection needle 16. Since in fact the container 12 contains enough fluid for a plurality of injections, for instance 100 units of insulin, the needle 16 should be replaced after each injection with a new, sterile needle; this is done by screwing a new needle 16 into the thread 21, and the rubber membrane 14 (FIG. 6) forms a tight seal again each time after the distal needle end 16 has been withdrawn.

A screw cap 25, knurled on the outside, that can be screwed onto a male thread 26 on the distal end of the holder sleeve 20 is used to close the distal end of the outer sleeve 20. This screw cap 25 is provided with a central recess 27 (FIGS. 2 and 4) through which the injection plunger or tappet can pass unhindered. On its proximal end, the screw cap 25 forms a shoulder 28 which is used as a spring support for a restoring spring 29. The holder sleeve 20 is made from a transparent plastic, to enable visual observation of the container 12 in order to tell how much fluid it still contains.

An important safety feature of the present invention is that the holder sleeve 20 can be adapted very precisely to the container (cartridge) 12 made by various manufacturers. This protects against mistakenly using the wrong container holding a higher dose, which could for instance lead to an insulin overdose for the patient and the well-known harmful results (coma).

The front, proximal housing part 30 is used to hold the holder sleeve 20 displaceably and is provided with a male thread 31 on its distal end for attaching it to the rear, distal housing part 32. It has windows 33, 33', 33" through which the contents of the container 12 can be observed The front housing part 30 may be made of metal, such as aluminum, or of some suitable plastic, such as polypropylene. In the region of its proximal end it is provided with a tactile ring 30', for instance for blind diabetics. As FIGS. 2 and 4 show, in its distal region the front housing part 30 has a cylindrical hollow chamber 34 of larger diameter, which via an annular shoulder 35 changes to a cylindrical hollow chamber 36 of smaller diameter The diameter of the hollow chamber 36 is only slightly larger than the outside diameter of the cylindrical holder sleeve 20, to allow axial displacement of the holder sleeve in the hollow chamber 36. In the assembled state, the spring 29 is located between the annular shoulder 28 on the screw cap 25 and the annular shoulder 35 and consequently urges the holder sleeve 20 in the distal direction. In the position of the device after an injection, the spring 29 is tensed, as FIG. 2 shows, and the tappet or plunger 18 rests against the piston 17 in a biassed manner and prevents the spring 29 from relaxing. If the tappet 18 is retracted, as FIG. 4 shows, then the spring 29 relaxes and presses the holder sleeve 20 in the distal direction as far as the stop, against a cylindrical sleeve 40 secured in the rear housing part 32. The sleeve 40 has a longitudinal slit 41 over the majority of its length, which is used to guide the tappet 18 longitudinally and is in alignment with a windowlike opening 42 in the rear, distal housing part 32—An adjusting nut 46, which is used to adjust the penetration depth of the needle 16 into the patient, is screwed into a female thread 45 on the proximal end of the front housing part 30.

To assemble the B part is, a new container 12 is first inserted, in the position shown in FIG. 6, into the holder sleeve 20, and the screw cap 25 is then screwed onto the male thread 26. Next, with an auxiliary device (not shown) surrounding the injection needle 16 in a sterile manner, the needle is screwed with its male thread 22 into the female thread 21 of the holder sleeve 20; the distal end 15 of the needle punctures the diaphragm 14 and penetrates into the fluid in the container 12. Then the holder sleeve 20 with the container 12 and needle 16 thereon is introduced through the distal end into the front housing part 30, in which the spring 29 is already present. To protect the injection needle 16, this housing part 30 may be provided with a protective sleeve or cap on its proximal end.

Once the front housing part 30 has been loaded in this way, it can be screwed with its thread 31 into a corresponding thread 48 of the rear housing part 32, and is for instance then ready for a plurality of injections in so-called intensified insulin therapy; that is, a plurality of injections at preselected dosages can be made from the container 12, depending on the insulin requirement of the patient. The way in which this is done will become apparent from the ensuing description of the A part.

It should also be noted here that the spring 29 is engaged at its distal end in an indentation 47 in the housing part 30, to prevent its being lost during use. Highly advantageously, this spring 29 is a spring having a very low spring constant; in other words, it is very soft. In the tensed state, in which the holder sleeve 20 rests with its proximal end against the adjusting nut 46, the spring 29—as shown—is not fully compressed; in this state its spring force is preferably approximately approximately 20 g, or at maximum 30 g. This is considered to be important for proper functioning of the injection device 10 described.

The sleeve 40 is secured in the rear housing part 32, as already described, with its longitudinal slit 41 in alignment with the window 42 of the housing part 32, so that through this window 42 one can see into the inside of the sleeve 40. The sleeve 40 is provided with an inwardly protruding collar 49 at its distal end.

On the outside of the housing part 32 and near its distal end, a ring 50 is formed; cf. FIGS. 25 and 26. It has a discontinuity 51, which as shown in FIG. 25 is located on the same generatrix as the window 42. This discontinuity is used to secure the clip 11 against twisting. To this end, the clip 11 protrudes into the discontinuity 51, as shown for instance in FIG. 3. The clip 11 is provided with a protrusion 53 projecting inwardly, which in the assembled state faces the window 42; see FIGS. 2-5. As will be described hereinafter, this protrusion 53 is used to initiate the injection process.

The clip 11, which may for instance be formed as an injection molded part made of polyamide, has a retaining ring 54, which rests against the ring 50 of the housing part 32 and encompasses a cylindrical portion 55 of the rear housing part 32.

Components that act as the "brain" of the device, and the function of which is to preclude mistakes in using the device, are secured in the interior of the rear housing part 32. With insulin injection, as already mentioned, such mistakes can be injurious to health, or may even cause coma.

The plunger or tappet 18 has an adjusting thread 60 on its outside, the shape of which (a steep thread) is shown three-dimensionally in FIG. 8. This thread 60 is guided in a corresponding female thread 61 of an adjusting sleeve 62. This female thread 61 is shown in FIGS. 2-5, 9, 11 and 14A.

The tappet 18 also has an axially extending longitudinal groove 63 on its outside, which is shown in FIGS. 2-5 and like the male thread 60 extends from the distal end of the tappet 18 almost to its proximal end. A radially inwardly projecting protrusion 65 of a guide element 66, which is shown on a greatly enlarged scale in FIGS. 21-24, protrudes into this longitudinal groove 63.

The guide element 66 has several functions. On its distal end, it is provided with three claw-like protrusions 67, which extend over an annular collar 68 on the proximal end of the adjusting sleeve 62 and are snapped into place behind the annular collar 68. As a result the guide element 66 is connected freely rotatably to the adjusting sleeve 62, yet can transmit axial forces from or to it. The guide element 66 is suitably formed from an elastic plastic, such as a polyamide; the claw-like protrusions 67 can therefore be snapped onto the annular collar 68 when the device is assembled. The internal bore 69 of the guide element 66 is smooth so that the guide element can slide on the tappet 18.

On its end remote from the protrusions 67, the guide element 66 also has a resilient latch member 70, which is provided with a pawl or protrusion 71 on its free end. The pawl 71 is axially guided in the longitudinal groove 41 of the sleeve 40 and thereby prevents rotation of the guide element 66 and of the tappet 18 axially guided in it, so that the tappet cannot twist relative to the rear housing part 32. Rotating the adjusting sleeve 62 causes the tappet 18 to be rotated either out of the adjusting sleeve 62 (thus increasing the overall length of the arrangement shown in FIG. 8) or into the adjusting sleeve 62 (making the arrangement shown in FIG. 8 shorter). Since the length of the arrangement shown in FIG. 8, comprising the tappet 18 and the adjusting sleeve 62, determines the injection quantity, this illustrates the principle by which the injection dose is set; for this purpose, an actuating knob 74 is secured to the male thread 73 on the distal end of the adjusting sleeve 62. The actuating knob 74 is used to cock the injection device 10 prior to the injection and also, in the cocked state, to set the amount of fluid to be injected, as will be described in detail hereinafter.

To prevent the possibility that the tappet 18 could be rotated all the way out of the adjusting sleeve 62, a securing screw 75 is screwed into the distal end of the tappet 18—after it has been mounted in the adjusting sleeve 62—and as shown, this screw serves as an axial stop. An axial stop of this type is also provided on the proximal end of the tappet 18, as shown.

As shown in FIGS. 2-5, the pawl 71 slides in the longitudinal groove 41 of the sleeve 40. If it arrives at the window 42 as the injection device 10 is cocked (by means of the actuating knob 74), it snaps into it and catches, as shown in FIGS. 5 and 4. By pressing on the clip 11, it can be retracted from the window 42, thereby initiating (triggering) the injection process.

As shown in FIG. 26, the rear housing part 32 has an inwardly protruding collar 78 on its distal end, and supported on this collar—via an interposed O-ring 79—is the collar 82 of a securing sleeve 83, which protrudes in the distal direction through the opening left open by the collar 78. A ratchet device 85 and a zero setting element 86 are secured on this sleeve 83 by means of two screws 84. If the zero setting element 86 is rotated, the ratchet device 85 and the sleeve 83 are rotated as well; the O-ring 79 acts as a slip coupling between the sleeve 83 and the rear housing part 32 and normally holds these parts firmly relative to the rear housing part 32, or in other words prevents them from rotating.

As can be seen from FIGS. 1-5, the zero setting element 86 is a thin-walled cylindrical part that when the injection device 10 is not cocked (FIG. 3) surrounds the actuating knob 74 with a slight clearance, but leaves a grip surface on the knob free. It has two windows: one window 87 on its distal end and another window 88 in the region of its proximal end. The actuating knob 74 has a setting scale 89 associated with these windows and provided with indicia for the injection quantity that has been set. For example, the "zero" marking is visible on the scale 89 in the window 88 in FIG. 1. The scale 89 is readable through the window 88 in the uncocked state; see FIG. 3. In the cocked state (see FIG. 5) it can be read through the window 87. Since the setting of the injection quantity can be done only in the cocked state (FIGS. 4 and 5), and the readout is done through the window 87, it is important that even after the injection the patient will still be able to read the amount he has just injected. This is accomplished very elegantly and simply by means of the two windows 87, 88 in combination with the scale 89, and in actual use this is an essential safety feature that until now was lacking in devices of this type. In other words, in known devices for this purpose, the injection dose was no longer readable after the injection process.

In the uncocked state, the ratchet device 85 is located in the interior of the actuating knob 74 and is located substantially concentrically to it and to the zero setting element 86. It is shown in detail in FIGS. 16-20; the three-dimensional view of FIG. 16 enables all its essential details to be understood.

The ratchet device 85, which is of an elastic plastic material such as a polyamide, has a cylindrical body 92, which is provided with two diametrically opposed threaded bores 93 for securing the screws 84 and has a recess 94 for holding the securing sleeve 83 in a fitting manner; see FIG. 5, for example. Axially in its approximate center, the ratchet device 85 has a groove 95 that extends vertically to the axial direction and partitions off a resiliently deflectable latch member 96, which as shown may be approximately 120° long and is provided with an inwardly protruding pawl 97 on its free end. As seen particularly well in FIG. 20, the latch member 96 with its pawl 97 is elastically deflectable radially outward. The axial length of the latch member 96 and pawl 97 is relatively short, as seen in FIGS. 16-18, and amounts to approximately 30% of the total length of the ratchet device arrangement 85.

As FIG. 7 shows, the pawl 97 cooperates with corresponding control recesses 100 on the outer surface of the adjusting sleeve 62. It should be noted in this connection that a kinematic reversal is of course possible, with the control recesses provided on the inside of the adjusting sleeve 62; in that case the ratchet device arrangement 85 would have to be disposed on the inside of the adjusting sleeve 62. For the sake of a compact shape, however, the embodiment shown is preferred. FIG. 7 is a three-dimensional view showing how the ratchet device 85 surrounds the adjusting sleeve 62. In operation, the ratchet device 85 and the adjusting sleeve 62 execute both axial and rotary movements relative to one another.

FIGS. 9-15 show the precise embodiment of a preferred exemplary embodiment of the adjusting sleeve 62. The annular collar 68 and the female thread 61 are located on the proximal end. The male thread 73 is located on the distal end. The annular collar 68 is succeeded by a cylindrical portion 103 of smaller diameter, which is succeeded in turn by an annular collar 104 serving as a spring support for a cocking spring 105. The cocking spring 105 is shown in the relaxed state in FIG. 8 and in the tensed (cocked) state in FIGS. 4, 5 and 7. It is used as an energy storing device for the injection process. Its other end rests on the collar 49 of the sleeve 40, as FIGS. 2-5 show.

The annular collar 104 is succeeded in the distal direction by a cylindrical portion 106, which has the same diameter as the cylindrical portion 103. It is succeeded by the portion having the control recesses 100.

The control recesses 100 have the following important function:

a) They allow cocking of the injection device 10 only when a predetermined value on the scale 89 is displayed in the window 88. In the exemplary embodiment, this value is the "zero" shown in FIG. 1. Only in this relative rotational position of the zero setting element 86 and the actuating knob 74 is cocking of the injection device possible at all; in all other rotational positions, contrarily, it is prevented.

b) Moreover, the control recesses 100 do not allow tripping of the device in this same zero position. This is important, because in the zero position, and only in the zero position, it would not be possible to prevent the injection of a small amount of fluid, i.e. in that case the figure displayed on the scale would not accurately reflect the actual situation.

c) The control recesses 100 do allow setting of the desired injection quantity in the cocked position, but only up to a predetermined maximum value, such as 17 units.

d) The control recesses 100 also allow initiation of an injection at any setting in which the injection quantity exceeds a predetermined minimum quantity.

e) The control recesses 100 place an upper limit on the injection quantity that can be set.

All this is accomplished by the cooperation of the control recesses 100 with the pawl 97 (FIGS. 16-20).

The control recesses 100 have a portion 110, which is used primarily to set the injection quantity and which is shown in cross section in FIG. 13; it is succeeded by a first barrier portion 111, then a cylindrical portion 112, a portion 113 of smaller diameter for the zero positioning in the uncocked state, and finally another cylindrical portion 114, which is provided with the male thread 73 on its distal end.

In the uncocked state, as shown in FIGS. 2 and 3, the pawl 97 is located in the portion 113 and substantially fills it, with its lateral edges 115 (FIG. 18) located opposite and spaced slightly apart from the lateral edges 116 (FIG. 11) of the portion 113. In this position, the adjusting sleeve 62 can be rotated by nearly 360° relative to the ratchet device 85, which is rigidly connected to the zero setting element 86.

An axially extending partitioning wall 117 (FIGS. 10 and 12) in the portion 113 acts as a stop and limiting device for such relative rotation and limits it to less than 360°. In this portion 113, as noted, such relative rotation is possible only in the uncocked state, which is shown in FIGS. 2 and 3.

To make it at all possible to slip the ratchet device 85 onto this adjusting sleeve 62, an axial longitudinal groove 122 is provided on the distal portion of the adjusting sleeve; this groove extends from the distal end of the adjusting sleeve 62 to the distal end of the portion 110, and its cross-sectional shape is shown in the upper part of FIG. 9. Its depth is constant up to the portion 111, decreases from about there in the proximal direction, and becomes zero in the distal region of the portion 110; see FIG. 9. The proximal end of this groove 122 is succeeded by a short cylindrical portion 123, and then a recess 124, which in longitudinal section—as shown in FIG. 9—has a rectangular cross section with perpendicular edges.

FIG. 15 shows part of the adjusting sleeve 62 in developed form. It can be seen that the pawl 97 is capable of moving through the groove 122 toward the left, or in the proximal direction, along the dot-dash line 121. (In actuality, the adjusting sleeve moves in the axial direction relative to the pawl 97.) If the pawl 97 reaches the cylindrical portion 123, it is deflected radially outward and then slides into the recess 124 and snaps into place there; accordingly it can no longer move in the distal direction. In this process the spring 105 is tensed, and the latch member 21, as shown in FIG. 5, snaps into the window 42.

The position in which the pawl 97 is in alignment with the longitudinal groove 122 corresponds to the zero injection quantity, as shown in FIG. 1 ("zero" is displayed in the window 88). Accordingly, cocking can be done only in this position; once the pawl 97 has snapped into the recess 124 after cocking, tripping of the device by actuation of the clip 11 is still possible but has no effect, because with the pawl 97 snapped into place in the recess 124, axial motion of the pawl 97 along the dot-dash line 121 is prevented. This prevents injection at the zero injection amount setting, for the reasons given above in paragraph a).

With reference to FIG. 13, the recess 124 is succeeded in the circumferential direction by a total of 18 ratchet teeth 126 spaced uniformly apart from one another. If the pawl 97 is located in the recess 124, then it can be moved, by rotating the setting knob 74, into one of the detent positions defined by the ratchet teeth 126, which corresponds to a predetermined rotation of the adjusting sleeve 62 relative to the housing part 32 and thus to screwing the tappet 18 out of the adjusting sleeve 62; in other words, the arrangement shown in FIG. 8 becomes longer in proportion to this rotation. This is indicated in FIG. 15 by the dot-dash line 128. If in this process the pawl assumes the position 97a, for instance, this is equivalent to a particular injection quantity, such as 10 I.U. of insulin. In this position, the injection device 10 can be tripped by pressing on the clip 11; the pawl 97a then executes a relative sliding motion along the dot-dash line 129, or in other words out of the detent recess into the conical portion 111, across the cylindrical portion 112, and back into the portion 113 where the pawl then assumes the position 97b. In that position, re-cocking is prevented by the fact that the pawl 97b abuts against the proximal edge 116 of the portion 113. If it should accidentally be possible to override this proximal edge 116, then the proximal edge 132 of the conical portion 111 acts as the next obstacle, so that cocking far enough that the pawl snaps into place is still prevented. This will remind even a blind diabetic that he has not yet reset his device, and that an injection is not possible. Double safety is attained by the edges or shoulders 116 and 132. (The edge 132 is not provided in the embodiments shown in FIGS. 2–5.) The ratchet teeth 126 enable adjustment only in the direction of increasing injection quantities, and their depth decreases in the distal direction, as shown, so that the pawl 97 can slide laterally out of them. If another injection is to be given, then the pawl 97 must first be rotated along the dot-dash line 133 until it abuts the partition wall 117, by rotating the zero setting element 86 and the ratchet device 85 rigidly connected to it. The scale 89 in the window 88 then displays the value "0", as in FIG. 1, and re-cocking becomes possible. It should be noted that this rotation of the zero setting element 86 does not change the position of the tappet 18 at all.

Setting the injection dose in the cocked state is possible only until the pawl 97 reaches a position in a recess 135, which is separated from the recess 124 by a partition wall 136. This partition 136 has perpendicular walls and therefore cannot be overridden by the pawl 97, which as shown in FIGS. 19 and 20 is likewise limited in the circumferential direction by perpendicular edges 137. Thus the partition 136 acts as a stop which places an upper limit on the injection dose, for instance of 17 I.U. (international units) of insulin. From this setting, the device can also be tripped.

Operation: First, the B part is loaded with a new cartridge 12, in the manner described at the outset above, and a new needle 16 is inserted. With the device in the tripped state, the tappet 18 is then screwed as far as possible into the adjusting sleeve 62 by rotating the adjusting sleeve 62 in the direction of the arrow 140 (FIG. 8), or in other words by rotating the knob 74 counterclockwise as seen from the distal end. Next, the housing part 30 and the housing part 32 are screwed together. With the device not yet cocked, the proximal end of the tappet 18 is now spaced apart by a distance from the piston 17 of the cartridge 12, and this distance must be reduced to zero. The actuating knob 74 is therefore rotated clockwise (as seen from the distal end of the device), together with the zero setting element 86, until the tappet 18 touches the piston 17, as is shown in FIG. 2. The user can tell this by the emergence of a drop of fluid from the needle 16.

The scale now indicates a high value, and therefore the next step is that the zero setting element 86 is rotated clockwise, by itself, until the scale displays the value "zero".

Now the injection device 10 can be cocked. To this end, the actuating knob 74 is retracted in the distal direction from the zero setting element 86, far enough that the pawl 71 snaps into the window 42 of the housing part 32. The position shown in FIG. 4 then pertains.

Next, the injection dose is set. To this end, the actuating knob 74—in its cocked position—is now rotated clockwise (as seen from the distal end) until the scale 89 displays the desired injection dose. A blind diabetic can also set the injection dose by counting the audible clicks produced during the setting. Each click may for instance represent one international unit. Thus the setting is humanly perceivable.

After the setting, the device 10 is placed with its proximal end on the desired part of the body that is to be injected, such as a hip. The clip 11 is then pressed, which forces the pawl 71 out of the window 42. The tensed spring 105 now relaxes and accelerates the tappet 18 in the proximal direction. The tappet 18 meets the piston 17. Since the piston 17 presents resistance to motion in the cartridge 12, the cartridge 12 is first moved along with its guide tube 20 in the proximal direction counter to the—weak—counterforce of the restoring spring 29, whereupon the needle 16 enters the patient. The guide tube 20 comes to rest on the (adjustable) stop 46 (the position of which is visible in the window 33''). Via the tappet 18, the force of the spring 105 now acts only upon the piston 17 and displaces it in the cartridge in the proximal direction, so that an amount of fluid that corresponds to this displacement—which was set by the user beforehand—is injected.

After the injection, the needle 16 is withdrawn from the patient's body and replaced with a new one and protected with a sterile cap. Then the scale is reset to zero by rotating the zero setting element 86 clockwise. Before the device is cocked again, a drop of fluid is first forced out of the needle 16, in order to check that the tappet 18 is in the correct position.

The device according to the invention makes it possible to give an injection even in parts of the body, such as the bottom, that for self-injection could not be reached with conventional syringes. With the invention, a number of arbitrarily dosable injections can be given from a single cartridge. Since the device according to the invention is quite small, the patient can carry it anywhere and can therefore continue intensified insulin therapy even on trips, for example. Practically foolproof use is made possible by the specialized design of the control recesses 100 in combination with the pawl 97. Of course, the patient must always be instructed carefully in the use of such injection devices in a clinical setting, and it is understood that a compromise will always be necessary between the size of such a device and its built-in functions.

Naturally, numerous modifications and changes are possible within the scope of the present invention.

One important safety feature is provided by the shape of the ratchet teeth 126 in combination with the ratchet device 85. In the cocked position (FIGS. 4, 5), because of the shape of these ratchet teeth 126, the actuating knob 74 can in fact be adjusted only in the direction of an increasing injection quantity; in other words, the path 128 in FIG. 15, like the paths 122 and 129, is a one-way street, so that in FIG. 15 the path is necessarily a kind of "traffic in a circle".

The slip coupling in the form of the O-ring 79 also plays an important role for safety because it retains the zero setting element 86 firmly, and releases it only at a relatively high breakaway torque. As a result, the zero setting element 86—and with it the ratchet device 85 rigidly joined to it—functions virtually like a part structurally connected to the housing, yet for zero setting of the scale after the injection it can be rotated easily and moved to a new zero position. Naturally, any other desired means may be used to generate this breakaway torque. The zero setting element might also be mechanically blocked as well, once the device 10 is cocked.

In the exemplary embodiment described above, correct use is assured by an arrangement that could also be called a mechanical computer. Within the scope of the invention, a microprocessor could naturally be used instead and could then process other input signals as well, such as for the fill level of the cartridge 12, for the presence of the needle 16, for checking for plausibility of the injection amount set, and so forth, and such a computer could then effect an automatic resetting to zero after an injection. Such a device would be relatively large and heavy, however, while the device of the embodiment is compact and requires no additional energy sources such as batteries, can be carried anywhere, and is easily sterilized.

We claim:

1. An injection device for performing dosed injections, said injection device defining a proximal end and a distal end and having
    an elongated housing (30, 32) for reception of an ampule or medication container (12) retaining a medicinal fluid,
    said ampule including a fluid expelling piston (17) movable in proximal direction within the ampule and having means for reception of an injection needle (16) engageable with the proximal end of the ampule and movable with the ampule in proximal direction with respect to the housing in an injecting direction;
    an injection plunger or tappet (18) engageable against said piston (17);
    a plunger length setting mechanism (62) coupled to said plunger and forming with said plunger an injection dosing arrangement (18-22).
    said plunger setting mechanism having two relatively rotatable parts, one of which is formed by said plunger (18), and means (40, 70, 71, 100) for preventing relative rotation of one of said parts with respect to said housing;
    a spring (105) coupled to the injection dosing arrangement (18-62);
    user operable spring cocking means (74);
    user operable spring release means (11, 53),
    said spring (105), after cocking, moving the injection dosing arrangement (18-62) upon release by the spring release means (11-53) longitudinally in the housing for engagement of said plunger (18) with said piston (17) to expel medicament fluid from the injection needle,
    and comprising
    locking means (100) operatively associated with said plunger length setting mechanism (18, 62) and effective only when said plunger length setting mechanism is in a distal terminal position, and to permit rotation of the other (62) of said parts relative to the housing only in a predetermined direction (FIG. 15: 128) with respect to the housing while inhibiting rotation in reverse direction, said locking means being ineffective when said plunger length setting mechanism is in a terminal proximal position.

2. The device of claim 1, wherein said spring cocking means (74) is rotatable with respect to the housing, said spring cocking means, upon rotation from a reference or zero position determining the dosage of medicinal fluid to be injected, said spring socking means forming, thereby, a dosage setting means; and
    means for resetting the dosage setting means to the reference or zero position after an injection to permit determining the dosage of a subsequent injection by rotation of said spring cocking means forming also the injection dosage setting means.

3. The device of claim 2, wherein said locking means (100) includes ratchet teeth (110) coupled to said plunger length setting mechanism (62), and a ratched pawl (97) operatively associated with the housing (85, 40) to permit rotation of said plunger length setting mechanism (62) only in said predetermined direction (FIG. 15: 120).

4. The device of claim 3, including an adjustment element (86), said adjustment element (86) being rotatable with respect to the housing (40) upon overcoming a predetermined minimum torque, said adjustment element being coupled to said pawl;
    said scale means (89) provided on said device to determine said zero or reference position after an injection has been effected.

5. The device of claim 3, further including a rotatable element (85, 86), relatively rotatable with respect to the housing, said pawl (97) being located on said rotatable element;
    a housing element (40) within the housing (30, 32); and
    a torque coupling (79) between the rotatable element and said housing sleeve (40), permitting, under force, override of a coupling connection between the rotatable element and the housing sleeve while carrying along the housing sleeve (40) upon rotation of the rotatable element and maintain the relative position of the rotatable element (85, 86) and the housing sleeve unless manually overridden.

6. The device of claim 5, wherein said high torque coupling comprises an O-ring (79).

7. The device of claim 1, including stop means (117, 136) effective and coupled to said plunger length setting mechanism (62) and limiting relative rotation of said plunger length setting mechanism with respect to the housing (40) when the plunger length setting mechanism is in either proximal or distal terminal position.

8. An injection device for performing dosed injections, said injection device defining a proximal end and a distal end and having
an elongated housing (30, 32) for reception of an ampules or medication container (12) retaining a medicinal fluid,
said ampule including a fluid expelling piston (17) movable in proximal direction within the ampule and having means for reception of an injection needle (16) engageable with the proximal end of the ampule and movable with the ampule in proximal direction with respect to the housing in an injecting direction;
an injection plunger or tappet (18) engageable against said piston (17);
a plunger length setting mechanism (62) coupled to said plunger and forming with said plunger an injection dosing arrangement (18-22),
said plunger setting mechanism having two relatively rotatable parts, one of which is formed by said plunger (18), and means (40, 70, 71, 100) for preventing relative rotation of one of said parts with respect to said housing;
a spring (105) coupled to the injection dosing arrangement (18-62);
user operable spring cocking means (74);
user operable spring release means (11, 53),
said spring (105), after cocking, moving the injection dosing arrangement (18-62) upon release by the spring release means (11-53) longitudinally in the housing for engagement of said plunger (18) with said piston (17) to expel medicament fluid from the injection needle,
wherein said spring cocking means (74) is rotatable with respect to the housing and forms a first setting element;
said device further having
a second setting element (86);
a control arrangement (85) depending on the position of the first setting element (74) relative to the second setting element (86), said control arrangement including an engagement element (85); and
a counterpart engagement element having a first and second portions (110, 113) coupled to said plunger length setting mechanism (62), said engagement element being engageable with the first portion (110) after cocking by said spring cocking means (74) and with the second portion (113) after the injection portion process.

9. The device of claim 8, further including stop means (117) coupled to said second portion (113) for engagement with said engagement element (85),
said stop means, upon engagement with said second portion (113), limiting the relative rotation between said spring cocking means (74) and the second element (86) to a predetermined angular range.

10. The device of claim 8, wherein said second portion includes a control recess (116, 122) for engagement with said engagement element (85) effective, after an injection process, to block axial cocking motion of said cocking means (74) beyond a predetermined relative rotational position between the engagement element (85) and said setting mechanism (62).

11. The device of claim 8, further including a scale display (89);
and wherein, in quiescent condition and before setting the dose for an injection, said scale display (89) shows a predetermined reference value, optionally a zero value.

12. The device of claim 8, wherein said plunger length setting mechanism (62) includes an annular groove (113) formed thereon;
said engagement element (85) being engaged against an edge of said groove, said edge (116) being formed with a recess (122) to permit axial cocking motion of the engagement element (85) upon movement of the cocking means (74) into cocked position only when in said predetermined angular position of said recess.

13. The device of claim 8, wherein said first portion (110) includes ratchet teeth (126) for engagement with said engagement element to permit incremental rotation between the first and second elements (74, 85) and enable humanly perceivable adjustment of the injection dose, by feel or hearing.

14. The device of claim 13, wherein said ratchet teeth (126) are shaped to permit, upon injection motion of said plunger length setting mechanism (16, 62), release of the engagement element (85) out of the ratched teeth (126).

15. The device of claim 8, further including stop means (136) engageable with the engagement element (85) and part of said first portion, to limit rotation between the engagement element and said plunger setting mechanism (62) to a predetermined angle of rotation to place an upper limit on the injection dose which can be set by said user operable spring cocking means (74).

16. The device of claim 8, including a scale display (87, 88, 89) provided between the second setting element (86) and said cocking means or first setting element (74), said scale display indicating the relative rotational position between said first and second setting elements and to form a display for an injection dose to be set.

17. The device of claim 8, further comprising a slip coupling (79) rotatably coupling the housing (32) to the second setting element (86),
said slip coupling being capable of slipping only above a predetermined minimum torque acting on the second setting element.

18. The device of claim 8, wherein said second setting element (86) at least in part surrounds the spring cocking means (74) to prevent a user from catching a finger between said first and second elements (74, 86).

19. The device of claim 18, wherein said first setting element is carrying scale markings on the circumference thereof; and
wherein the second setting element (86) includes at least one recess through which the scale markings are visible when said first setting means or cocking element (74) is in either cocked or uncocked state and, optionally, with two recesses to permit the scale markings to be visible regardless of the cocked or uncocked state of said first setting means (74).

20. The device of claim 8, wherein said plunger length setting mechanism comprises a threaded spindle (18) and a tubular element (62) formed with an internal thread, whereby, upon relative rotation of said spindle and said tubular element, the length of the plunger length setting mechanism including the plunger and the tubular element can be varied;

a guide element (66) is provided, optionally of plastic, rotatably secured to that end portion of the tubular element (62) facing the threaded spindle;

a longitudinal groove (63) formed in the threaded spindle;

and means for guiding said threaded spindle in the housing (30, 32) in longitudinal direction, said guide element (66) being snap-connected on the respective end portion (104) of said tubular element (62).

21. The device of claim 20, wherein said guide element (66) is formed with a radial extension (70, 71) longitudinally movable within the housing (30, 32), said extension (70, 71) forming a latch member which, in cocked position of the user operable spring cocking means, engages within a recess (42) of the housing to retain said plunger length setting mechanism (18, 62) in cocked position.

22. The device of claim 21, further including a tripping mechanism engageable through said recess (42) in the housing, and externally operable from outside of the housing, to release the latch member (70, 71), and hence initiate an injection process, said release member, optionally, including a fastening clip, and forming said user operable spring release means (11).

* * * * *